United States Patent
Kim et al.

(10) Patent No.: US 10,317,483 B2
(45) Date of Patent: Jun. 11, 2019

(54) RADIO FREQUENCY COIL FOR MAGNETIC RESONANCE IMAGING AND MAGNETIC RESONANCE IMAGING SYSTEM

(71) Applicant: Samsung Electronics Co., Ltd., Suwon-si (KR)

(72) Inventors: Kyoungnam Kim, Incheon (KR); Jung Hee Lee, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 130 days.

(21) Appl. No.: 15/322,685

(22) PCT Filed: Apr. 10, 2015

(86) PCT No.: PCT/KR2015/003595
§ 371 (c)(1),
(2) Date: Dec. 28, 2016

(87) PCT Pub. No.: WO2016/003059
PCT Pub. Date: Jan. 7, 2016

(65) Prior Publication Data
US 2017/0160354 A1 Jun. 8, 2017

(30) Foreign Application Priority Data
Jun. 30, 2014 (KR) .................. 10-2014-0081210

(51) Int. Cl.
*G01R 33/34* (2006.01)
*A61B 5/055* (2006.01)
*G01R 33/46* (2006.01)
*G01R 33/54* (2006.01)
*G01R 33/3415* (2006.01)

(52) U.S. Cl.
CPC ............. *G01R 33/34* (2013.01); *A61B 5/055* (2013.01); *G01R 33/3415* (2013.01); *G01R 33/4608* (2013.01); *G01R 33/4616* (2013.01); *G01R 33/4625* (2013.01); *G01R 33/54* (2013.01)

(58) Field of Classification Search
CPC ........................ G01R 33/34; G01R 33/3415; G01R 33/4608; G01R 33/4616; G01R 33/4625; G01R 33/54
See application file for complete search history.

(56) References Cited

U.S. PATENT DOCUMENTS

| 7,733,088 B2 | 6/2010 | Cho et al. |
| 2008/0100297 A1 | 5/2008 | Ishii et al. |

(Continued)

FOREIGN PATENT DOCUMENTS

| JP | 10-24025 A | 1/1998 |
| JP | 2013-106862 A | 6/2013 |
| KR | 2009-0053181 A | 5/2009 |

OTHER PUBLICATIONS

Machine Translation JP 10-024025 A obtained on Jul. 19, 2018.*
(Continued)

*Primary Examiner* — Gregory H Curran
(74) *Attorney, Agent, or Firm* — NSIP Law

(57) ABSTRACT

In a radio frequency (RF) coil for a magnetic resonance imaging (MRI) system, the RF coil includes loops that are radially arranged. At least some areas of each of the loops overlap each other at a central portion of a radial structure formed by the loops.

15 Claims, 5 Drawing Sheets

(56) References Cited

U.S. PATENT DOCUMENTS

| | | |
|---|---|---|
| 2008/0238424 A1 | 10/2008 | Possanzini |
| 2009/0212774 A1 | 8/2009 | Bosshard et al. |
| 2010/0033177 A1 | 2/2010 | Ochi et al. |
| 2015/0323624 A1* | 11/2015 | Feinberg ............ G01R 33/3685 324/309 |

OTHER PUBLICATIONS

International Search Report dated Jun. 30, 2015 in counterpart International Application No. PCT/KR2015/003595 (2 pages in English).

* cited by examiner

US 10,317,483 B2

RADIO FREQUENCY COIL FOR MAGNETIC RESONANCE IMAGING AND MAGNETIC RESONANCE IMAGING SYSTEM

CROSS-REFERENCE TO RELATED APPLICATIONS

This application claims the benefit under 35 USC 119(a) of PCT Application No. PCT/KR2015/003595, filed on Apr. 10, 2015, which claims the benefit of Korean Patent Application No. 10-2014-0081210 filed Jun. 30, 2014, in the Korean Intellectual Property Office, the entire disclosure of which is incorporated herein by reference for all purposes.

TECHNICAL FIELD

One or more embodiments of the present disclosure relate to a radio frequency (RF) coil for magnetic resonance imaging (MRI) and a MRI system.

BACKGROUND ART

A magnetic resonance imaging (MRI) device, a magnetic resonance spectroscopy (MRS) device, etc. are well known as a magnetic resonance system using nuclear magnetic resonance (NMR) phenomena.

An MRI device captures images of cross-sections of a human body by using NMR phenomena. Since atomic nuclei such as hydrogen (1H), phosphorous (31P), sodium (23Na), and carbon isotopes (13C) existing in a human body each have a unique rotating field constant due to the NMR phenomena, a high frequency signal is applied to magnetization vectors of the atomic nuclei arranged in a direction of a main magnetic field by using a RF coil, and the images of the cross-sections of the human body may be obtained as the RF coil receives a magnetic resonance signal generated when the magnetization vectors are rearranged on a vertical plane due to frequency resonance.

The RF coil includes a RF antenna that transmits high frequency signal and receives a magnetic resonance signal to resonate the magnetization vectors. The resonance of the magnetization vectors by using one RF coil (the RF antenna) (i.e., a RF transmission mode) and receiving the magnetic resonance signal (i.e., a RF receiving mode) may be simultaneously performed. Alternatively, a RF coil only for the RF transmission mode and a RF coil only for the RF receiving mode are separately used to separately perform the RF transmission mode and the RF receiving mode. A coil that performs both the RF transmission mode and the RF receiving mode is referred to as a transmit/receive (Tx/Rx) coil. A Tx only coil is referred to as a transmission coil, and a Rx only coil is referred to as a receiving coil. RF transmission coils are mostly installed within a main magnet and are in a cylindrical form or a birdcage form above a cylindrical frame which has a sufficient size to fit a human body therein. On the contrary, RF receiving coils may be located close to the human body and be in various forms, depending on shapes of body parts.

DETAILED DESCRIPTION OF THE INVENTION

Technical Problem

One or more embodiments of the present disclosure provide a radio frequency (RF) coil for magnetic resonance imaging (MRI) and an MRI system.

Technical Solution

A radio frequency (RF) coil for magnetic resonance imaging (MRI) includes: a plurality of loops radially arranged. At least some areas of each of the plurality of loops overlap each other at a central portion of a radial structure formed by the plurality of loops.

The RF coil may include a receive (Rx) only RF coil configured to obtain magnetic resonance signals resulting from excitation by RF signals.

Each of the plurality of loops may be connected to a separate RF channel.

The plurality of loops may be formed by using one lead wire connected to one RF channel, and each of the plurality of loops may be formed by coiling a portion of the lead wire once and having both ends of the portion cross each other.

The plurality of loops may be arranged in a horizontal direction on a same plane.

The plurality of loops may be arranged isometrically to form the radial structure.

A magnetic resonance imaging (MRI) system includes: a radio frequency (RF) coil assembly including a transmit (Tx) only RF coil configured to transmit a RF signal to a subject and a receive (Rx) only RF coil configured to obtain a magnetic resonance signal from a region of interest (ROI) of the subject, the magnetic resonance signal resulting from excitation by the transmitted RF signal; a RF coil controller configured to control a RF transmission mode of the Tx only RF coil and a RF receiving mode of the Rx only RF coil; and an image processor configured to generate an MRI image of the subject based on the obtained magnetic resonance signal, wherein the Rx only RF coil may include a plurality of loops that are radially arranged, and at least some areas of each of the plurality of loops overlap each other at a central portion of a radial structure formed by the plurality of loops.

Each of the plurality of loops may be connected to a separate RF channel.

The plurality of loops may be formed by using one lead wire connected to one RF channel, and each of the plurality of loops may be formed by coiling a portion of the lead wire once and having both ends of the portion cross each other.

The plurality of loops may be arranged in a horizontal direction on a same plane.

The plurality of loops may be arranged isometrically to form the radial structure.

The Tx only RF coil and the Rx only RF coil may overlap each other in parallel.

These and/or other aspects will become apparent and more readily appreciated from the following description of the embodiments, taken in conjunction with the accompanying drawings.

Advantageous Effects of the Invention

A radio frequency (RF) coil for magnetic resonance imaging (MRI) and an MRI system have improved B1 field sensitivity in a region of interest (ROI).

BEST MODE

Figure 1:
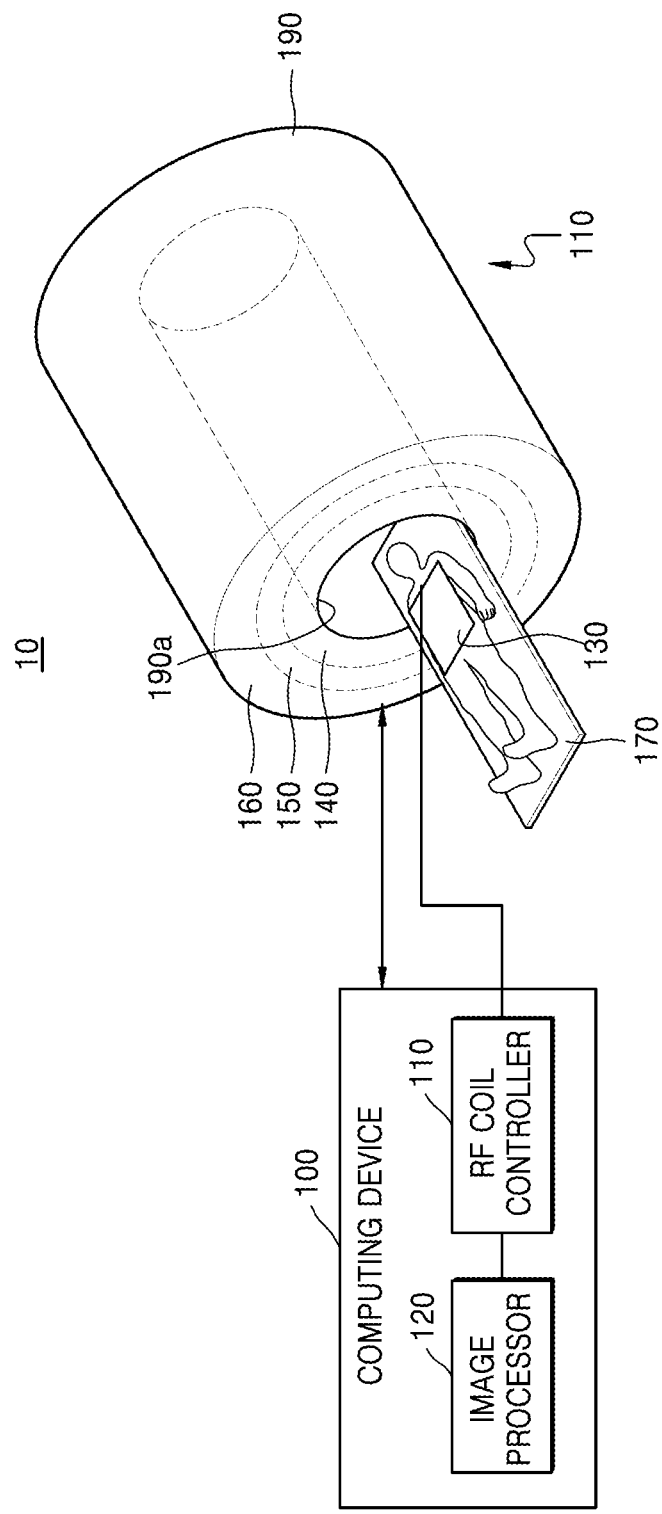
FIG. 1 shows a structure of a magnetic resonance imaging (MRI) system 10 according to an embodiment.

As the present disclosure allows for various changes and numerous embodiments, particular embodiments will be illustrated in the drawings and described in detail in the written description. The attached drawings for illustrating embodiments of the present disclosure are referred to in order to gain a sufficient understanding of the present disclosure, the merits thereof, and the objectives accomplished by the implementation of the present disclosure. The present disclosure may, however, be embodied in many different forms and should not be construed as being limited to the embodiments set forth herein.

Hereinafter, the present disclosure will be described in detail by explaining embodiments of the invention with reference to the attached drawings. Like reference numerals in the drawings denote like elements.

An expression used in the singular encompasses the expression of the plural, unless it has a clearly different meaning in the context. In the present specification, it is to be understood that the terms such as "including", "having", and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Sizes of components in the drawings may be exaggerated for convenience of explanation. In other words, since sizes and thicknesses of components in the drawings are arbitrarily illustrated for convenience of explanation, the following embodiments are not limited thereto.

FIG. 1 shows a structure of a magnetic resonance imaging (MRI) system 10 according to an embodiment.

Referring to FIG. 1, the MRI system 10 includes a computing device 100 and a cylindrical housing 190.

The cylindrical housing 190 includes a transmit (Tx) only volume-type RF coil device 140, a gradient coil 150, and a main magnet 160 in an order as stated from inside of the cylindrical housing 190 to outside thereof. A subject lying on a table 170 is moved into a bore 190a of the cylindrical housing 190, and then an MRI image is captured.

In the MRI system 10, the Tx only volume-type RF coil device 140, the gradient coil 150, and the main magnet 160 of the cylindrical housing 190 are connected to the computing device 100 and then driven and controlled by the computing device 100. The computing device 100 may be connected to a console (not shown) used to display the captured MRI image of the subject or receive a manipulation signal of a user.

In the MRI system 10, the Tx only volume-type RF coil device 140 may be independently driven or controlled by a RF coil controller 110 of the computing device 100 together with a RF coil assembly 130 of FIG. 1 installed on a body portion of the subject that is to be subject to examination.

The main magnet 160 generates a main magnetic field for magnetizing atom nuclei of elements, that is, hydrogen, phosphorous, sodium, carbon, and the like, which cause magnetic resonance phenomena among elements existing in the human body. The main magnet 160 may be a superconducting electromagnet or a permanent magnet.

The gradient coil 150 generates a spatially-linear gradient magnetic field to produce MRI images. In general, three gradient coils are used in the MRI images, each of which produces a gradient magnetic field in each of an x direction, a y direction, and a z direction. The gradient coil 150 spatially controls a rotation frequency or a phase of a magnetization vector when the magnetization vector rotates on a transverse plane, thereby indicating an MRI signal in a spatial frequency area, that is, a k area.

Magnetization vectors need to be arranged on the transverse plane in order to generate an MRI signal. To this end, the volume-type RF coil device 140 and the RF coil assembly 130, which generate a RF magnetic field where a Larmor frequency is a main frequency, are required. The volume-type RF coil device 140 and the RF coil assembly 130, to which a RF current in a Larmor frequency band is applied, generate a rotating magnetic field that rotates in the Larmor frequency. When resonance of the magnetization vectors, that is, nuclear magnetic resonance (NMR), is produced due to the rotating magnetic field, the magnetization vectors are arranged on the transverse plane. Once the magnetization vectors are arranged on the transverse plane, the magnetization vectors rotating on the transverse plane in the Larmor frequency produce an electromotive force in the volume-type RF coil device 140 and the RF coil assembly 130 according to Faraday's Law. When electromotive signals, that is, received RF signals, are amplified by a high frequency amplifier and then demodulated by a sine wave of the Larmor frequency, magnetic resonance signals in a base band may be obtained. The magnetic resonance signals in the base band are transmitted to the computing device 100, and an MRI image is produced by an image processor 120 through processes such as quantization.

A general principle for generating an MRI image by using the MRI system 10 has been briefly described. A process of generating an MRI image will be obvious to one of ordinary skill in the art, and thus a detailed description thereof will be omitted.

In the MRI system 10, the volume-type RF coil device 140 included in the cylindrical housing 190 may be used to capture an MRI image of an entire body of the subject. Unlike the volume-type RF coil device 140, the RF coil assembly 130 placed on a body part of the subject may be used to capture an MRI image of body parts of the subject, for example, the head, the chest, legs, or the like. The RF coil assembly 130 is a separate device installed outside the cylindrical housing 190 and is movable to be placed on a body part of the subject, an image of which is desired to be captured through the MRI.

A birdcage coil, a saddle coil, a transverse electromagnetic (TEM) coil, an Rx only surface coil, etc. are well known as RF coils installed on a body part of the subject.

Resonance frequencies operating in the MRI system 10 may vary. When the MRI system 10 operates at 3 tesla (3T), the MRI system 10 has an operating frequency of 127.74 MHz. When the MRI system 10 operates at 4.7T, the MRI system 10 has an operating frequency of 200 MHz. When the MRI system 10 operates at 7T, the MRI system 10 has an operating frequency of 300 MHz. When the MRI system 10 operates at 9.4T, the MRI system 10 has an operating frequency of 400 MHz.

However, when the MRI system 10 operates in an ultra high magnetic field at at least 7T and the RF coil assembly 130 is used for both reception and transmission via one RF coil, homogeneity of a B1 magnetic field that is generated by the one RF coil may decrease.

Thus, the MRI system 10, in particular, the RF coil assembly 130, may increase the homogeneity of the B1 magnetic field that is generated by the RF coil assembly 130 in an ultra high magnetic field at at least 7T by separating the Tx only RF coil and the Rx only RF coil from each other. The Tx only RF coil and the Rx only RF coil may overlap each other in a 2 dimensional (2D) space. However, the present disclosure is not limited thereto.

FIGS. 2 to 6 show the Rx only RF coil 131 according to one or more embodiments. The Rx only RF coil 131 obtains magnetic resonance signals resulting from excitation by RF signals.

Figure 2:
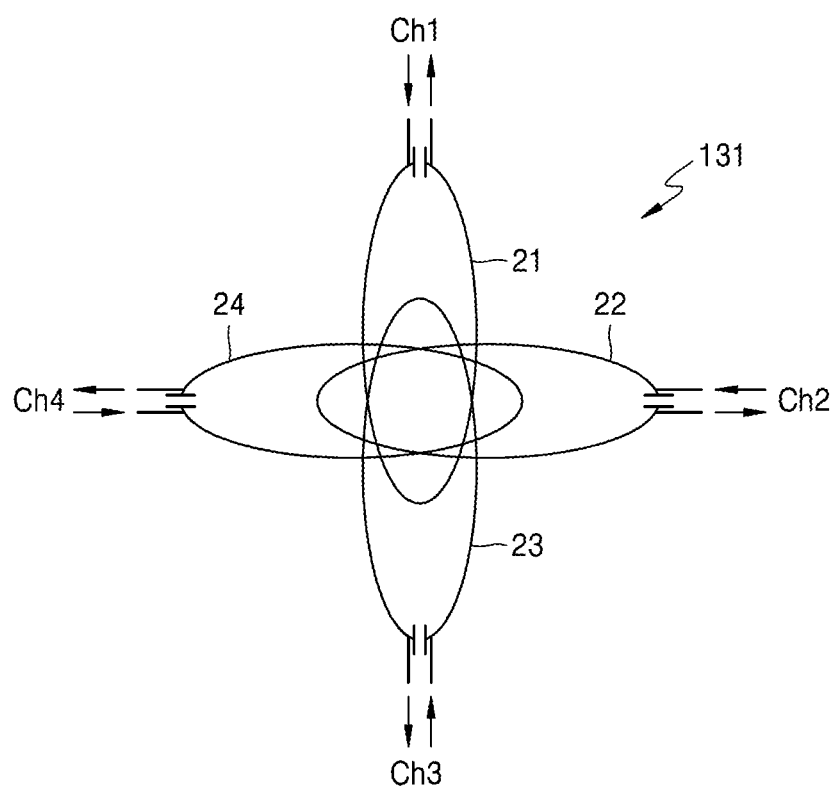
FIGS. 2 to 6 show a receive (Rx) only radio frequency (RF) coil 131 according to one or more embodiments.
Figure 3:
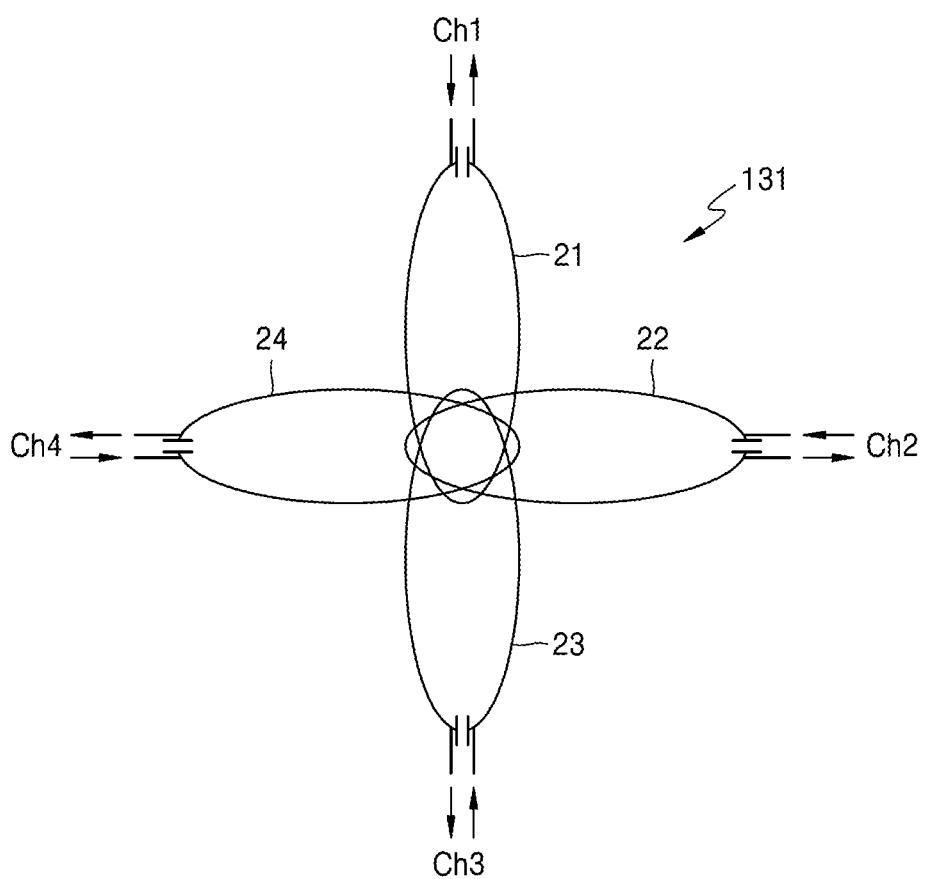

Referring to FIGS. 2 and 3, the Rx only RF coil 131 includes loops 21 to 24. The loops 21 to 24 may be radially arranged. Referring to FIG. 2, at least some areas of each of the loops 21 to 24 may overlap each other at a central portion of a radial structure formed by the loops 21 to 24. The loops 21 to 24 may each be connected to a separate RF channel. For example, the first loop 21 may be connected to a first channel ch1, the second loop 22 to a second channel ch2, the third loop 23 to a third channel ch3, and the fourth loop 24 to a fourth channel ch4.

Sizes of areas of the loops 21 to 24 that overlap each other at the central portion may differ, depending on specifications required for the MRI system 10. For example, according to a size of a region of interest (ROI) of the subject in the MRI system 10, overlapping areas of the RF coil 131 may increase or decrease. For example, as the size of the ROI increases, the overlapping area of the RF coil 131 may increase. The size of the overlapping area may have an influence on a signal-to-noise ratio (SNR). For example, the SNR increases as the size of the overlapping area decreases. Therefore, depending on specifications of the SNR required in the MRI system 10, the RF coil 131 having an overlapping area that is an appropriate size may be used.

Figure 4:
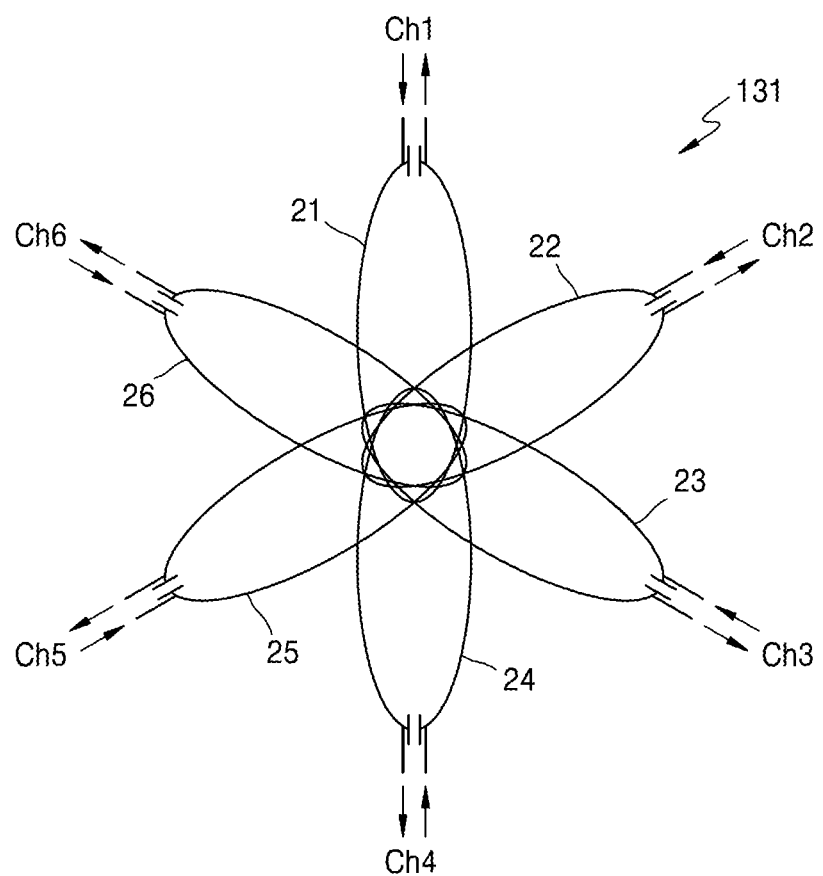

Referring to FIG. 4, the Rx only RF coil 131 includes loops 21 to 26. The loops 21 to 26 may be radially arranged. Referring to FIG. 4, at least some areas of each of the loops 21 to 26 may overlap each other at the central portion of the radial structure. The loops 21 to 26 may each be connected to a separate RF channel. For example, the first loop 21 may be connected to the first channel ch1, the second loop 22 to the second channel ch2, the third loop 23 to the third channel ch3, the fourth loop 24 to the fourth channel ch4, the fifth loop 25 to a fifth channel ch5, and the sixth loop 26 to a sixth channel ch6. The number of loops included in the Rx only RF coil 131 is not limited to the number described with reference to FIGS. 2 to 4. The number of loops included in the Rx only RF coil 131 may vary according to the use of the Rx only RF coil 131 and a design of the MRI system 10. For example, sensitivity of the Rx only RF coil 131 may differ according to the number of loops.

Accordingly, the number of loops included in the Rx only RF coil 131 may be determined based on the sensitivity of the Rx only RF coil 131 required in the MRI system 10 according to an embodiment. For example, when sensitivity needs to be increased in the central portion, a RF coil 131 including a large number of loops may be used.

Figure 5:
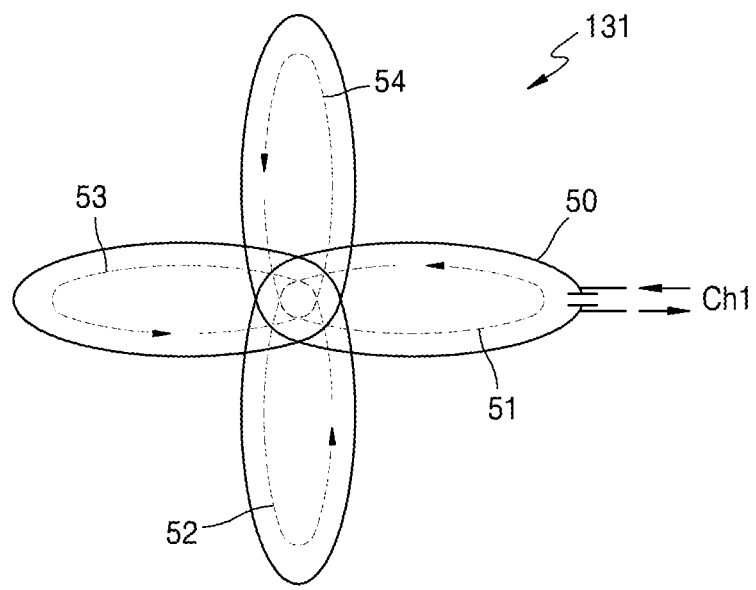

Referring to FIG. 5, the Rx only RF coil 131 includes loops 51 to 54. The loops 51 to 54 may be radially arranged. Referring to FIG. 5, at least some areas of each of the loops 51 to 54 may overlap each other at the central portion of the radial structure. The loops 51 to 54 may each be formed by coiling a portion of a lead wire 50 once and then having both ends of the portion cross each other. The loops 51 to 54 may be formed by one lead wire 50 connected to a RF channel, for example, the first channel ch1. That is, the loops 51 to 54 may be formed by coiling one lead wire several times and may be connected to one channel, for example, the first channel ch1.

As shown in FIGS. 3 and 4, the Rx only RF coil 131 connected to multiple channels may be used in an MRI system including an unlimited number of channels. If an MRI system includes a limited number of channels, a single-channel RF coil 131 may be used as shown in FIG. 5.

Figure 6:
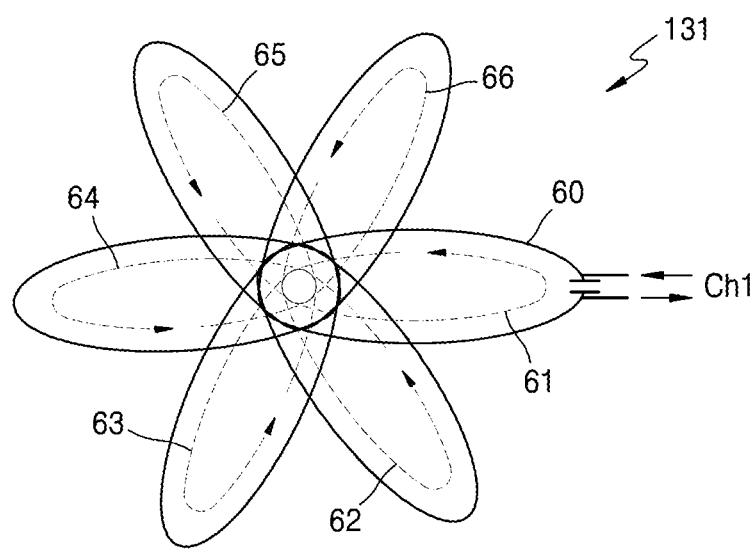

Referring to FIG. 6, the Rx only RF coil 131 includes loops 61 to 66. The loops 61 to 66 may be radially arranged. Referring to FIG. 6, at least some areas of each of the loops 61 to 66 may overlap each other at the central portion of the radial structure. The loops 61 to 66 may each be formed by coiling a portion of a lead wire 60 once and then having both ends of the portion cross each other. The loops 61 to 66 may be formed by one lead wire 60 connected to a RF channel, for example, the first channel ch1. That is, the loops 61 to 66 may be formed by coiling one lead wire several times, and the loops 61 to 66 may be connected to one channel, for example, the first channel ch1.

Referring to FIGS. 5 and 6, multiple loops may be formed by using a lead wire connected to a channel and may be arranged in such a manner that at least some areas of respective loops overlap each other at a central portion. Thus, even in an MRI system including a limited number of channels, a desired number of loops may be formed.

Although not shown in the drawings, the Rx only RF coil 131 may include loops, which are formed by using one lead wire and are connected to one channel, and loops which are formed by using different lead wires and connected to different channels.

MODE OF THE INVENTION

Referring to FIGS. 2 to 6, the loops included in the Rx only RF coil 131 may be arranged in a horizontal direction on a same plane. The Rx only RF coil 131 may be a flat coil.

Referring to FIGS. 2 to 6, the loops included in the Rx only RF coil 131 may be arranged isometrically to form a radial structure.

Referring to FIGS. 2 to 6, when the Rx only RF coil 131 that is an array coil in which multiple loops overlap is used, sensitivity of a B1 field and a RF excitation field (B1+) may increase in a region of interest (ROI) of an image. When multiple coils overlap one another at a central portion of the Rx only RF coil 131 having the radial structure, a strong RF field is formed in the central portion of the Rx only RF coil 131, and relatively weak RF fields are formed in other portions of the Rx only RF coil 131.

In the Rx only RF coil 131 according to an embodiment, as the number, shapes, locations of loops, an area of overlapping areas where loops overlap one another, etc. are variously set, the specification required in the MRI system 10, for example, B1 sensitivity desired in the ROI, may be embodied. When the number of channels is limited when setting the number of loops, a number of loops may be formed by using a lead wire connected to a channel, as shown in FIGS. 5 and 6.

While this present disclosure has been particularly shown and described with reference to embodiments thereof, it will be understood by those of ordinary skill in the art that various changes in form and details may be made therein without departing from the spirit and scope of the present disclosure as defined by the appended claims. The embodiments should be considered in a descriptive sense only and not for purposes of limitation. Therefore, the scope of the present disclosure is defined not by the detailed description of the present disclosure but by the appended claims, and all differences within the scope will be construed as being included in the present disclosure.

INDUSTRIAL APPLICABILITY

The present disclosure may be applied to a radio frequency (RF) coil for magnetic resonance imaging (MRI) and a MRI system.

The present disclosure has been described with reference to example embodiments thereof. Numerous modifications and adaptations will be readily apparent to one of ordinary skill in the art without departing from the spirit and scope of the present disclosure.

The invention claimed is:

1. A radio frequency (RF) coil for magnetic resonance imaging (MRI), comprising:
    a plurality of radially arranged loops collectively forming a structure,
    wherein at least one loop of the plurality of loops overlaps another loop of the plurality of loops at a central portion of the structure, and
    wherein an intersection between an opposing pair of loops of the plurality of loops is surrounded by at least two other loops of the plurality of loops.

2. The RF coil of claim 1, wherein the structure constitutes a receive (Rx) only RF coil configured to obtain magnetic resonance signals resulting from excitation by RF signals.

3. The RF coil of claim 1, wherein each of the plurality of loops is connected to a separate RF channel.

4. The RF coil of claim 1, wherein each of the plurality of loops is formed by coiling a portion of a lead wire connected to an RF channel once and having two ends of the portion cross each other.

5. The RF coil of claim 1, wherein the plurality of loops are arranged on a common plane.

6. The RF coil of claim 1, wherein the plurality of loops are arranged isometrically to form the structure.

7. The RF coil of claim 1, wherein
    the plurality of loops comprise a first loop, a second loop, a third loop, and a fourth loop,
    the first loop intersects the third loop at a first intersection and a second intersection,
    the second loop intersects the fourth loop at a third intersection and a fourth intersection,
    the first intersection and second intersection are surrounded by the second loop, and surrounded by the fourth loop, and
    the third intersection and fourth intersection are surrounded by the first loop, and surrounded by the third loop.

8. The RF coil of claim 1, wherein the plurality of loops are radially offset from one another by 60° about a center of the radial symmetry, and each loop of the plurality of loops overlaps every other loop of the plurality of loops.

9. The RF coil of claim 1, wherein a single wire continuously forms each of the loops.

10. A magnetic resonance imaging (MRI) system, comprising:
    a transmit (Tx) only RF coil configured to transmit an RF signal to a subject;
    a receive (Rx) only RF coil configured to obtain a magnetic resonance signal from a region of interest (ROI) of the subject, the magnetic resonance signal resulting from excitation by the transmitted RF signal;
    a RF coil controller configured to control an RF transmission mode of the Tx only RF coil and an RF receiving mode of the Rx only RF coil; and
    an image processor configured to generate an MRI image of the subject based on the obtained magnetic resonance signal,
    wherein the Rx only RF coil comprises a plurality of radially arranged loops collectively forming a structure,
    wherein at least one loop of the plurality of loops overlaps another loop of the plurality of loops at a central portion of the structure, and
    wherein an intersection between an opposing pair of loops of the plurality of loops is surrounded by at least two other loops of the plurality of loops.

11. The MRI system of claim 10, wherein each of the plurality of loops is connected to a separate RF channel.

12. The MRI system of claim 10, wherein each of the plurality of loops is formed by coiling a portion of a lead wire connected to an RF channel once and having two ends of the portion cross each other.

13. The MRI system of claim 10, wherein the plurality of loops are arranged on a common plane.

14. The MRI system of claim 10, wherein the plurality of loops are arranged isometrically to form the structure.

15. The MRI system of claim 10, wherein the Tx only RF coil and the Rx only RF coil overlap each other in a 2-dimensional plane.

* * * * *